United States Patent [19]

Wareing

[11] 4,321,269

[45] Mar. 23, 1982

[54] 1-(3-HALO-1,2-DIOXOPROPYL)-CYCLOAMINE COMPOSITIONS AND USE

[75] Inventor: James R. Wareing, Randolph, N.J.

[73] Assignee: Sandoz, Inc., E. Hanover, N.J.

[21] Appl. No.: 218,746

[22] Filed: Dec. 22, 1980

Related U.S. Application Data

[63] Continuation-in-part of Ser. No. 138,091, Apr. 7, 1980, abandoned.

[51] Int. Cl.$^3$ .............................................. A01N 43/40
[52] U.S. Cl. ...................................... 424/267; 424/244; 424/248.57; 424/246; 424/250; 424/274
[58] Field of Search .................. 424/244, 248.57, 246, 424/250, 267, 274

[56] References Cited

PUBLICATIONS

Winterfeldt et al., Ber, 101, (1968), pp. 3163-3171.

Primary Examiner—Henry R. Jiles
Assistant Examiner—R. W. Ramsuer
Attorney, Agent, or Firm—Gerald D. Sharkin; Richard E. Vila; Frederick H. Weinfeldt

[57] ABSTRACT

The compounds are 1-(3-halo-1,2-dioxopropyl)-cycloamines, eg 1-(3-chloro-1,2-dioxopropyl)-piperidine, and are useful as fungicides and bactericides. They can be prepared by halogenation of a corresponding 1-(1,2-dioxopropyl)-cycloamine.

19 Claims, No Drawings

1-(3-HALO-1,2-DIOXOPROPYL)-CYCLOAMINE COMPOSITIONS AND USE

This is a continuation-in-part of copending application Ser. No. 138,091 filed Apr. 7, 1980 (now abandoned).

This invention relates to cycloamine derivatives, and more particularly to 1-(3-halo-1,2-dioxopropyl)cycloamines, and to their use as fungicides and bactericides particularly in agriculture, as well as to fungicidal and bactericidal compositions containing such compounds.

The compounds of this invention may conveniently be represented by the formula I:

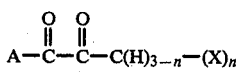

wherein
n is a whole integer of from 1 to 3, preferably 1;
X is halo having an atomic weight of from about 34 to 80, ie chloro or bromo; and
A is:

(a) 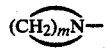

in which m is a whole integer of from 4 to 8 eg. 4 to 7;

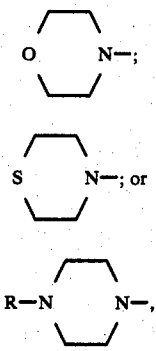

in which R is a hydrogen atom, or alkyl having from 1 to 4 carbon atoms.

Compounds I are obtainable by halogenation of a corresponding compound II:

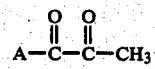

in which A is as defined above. The halogenation (process a) may be accomplished in the conventional manner for replacing methyl hydrogen atoms with chlorine or bromine atoms, eg by treatment with sulfuryl chloride (where x=Cl) or bromine (where X=Br). The halogenation may be carried out at moderate temperatures eg from about 0° to 60° C. An inert solvent such as a halogenated hydrocarbon, eg chloroform, may be employed as solvent.

Since in Compounds I n can be from 1 to 3, in preparing compounds I the number of equivalents of the halogenating agent required corresponds to the n desired. However, in general, an excess of the halogenating agent over that theoretically required is used, and the reaction is run until a significant amount of the desired product is formed.

Compounds II are obtainable by reacting a corresponding bis amide of the formula III:

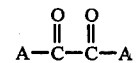

in which A is as defined above, with a methyl-contributing-organometallic reagent of the formula IV:

in which M is an alkali metal, or a magnesium halide, in an inert medium, under essentially anhydrous conditions (process b), to obtain an adduct, which is then hydrolyzed (process b') to the corresponding compound II.

Process (b) may conveniently be carried out in the conventional manner for carrying out a Grignard-type reaction. The M moiety of the compound used may be an alkali metal, e.g. Li, however, the preferred organometallic reagents include Grignard reagents, such as methyl magnesium halides, particularly methyl magnesium chloride. Suitable inert media include ethers, such as tetrahydrofuran or diethyl ether, and the reaction is preferably carried out at moderate temperatures of, for example, −10° to +20° C. The subsequent hydrolysis may be carried out in conventional manner for hydrolyzing a Grignard-type adduct, for example, with an aqueous acid such as dilute hydrochloric acid. When, in a compound of formula III, A is an unsubstituted piperazino radical, an additional two equivalents of the organometallic reagent are preferably used.

Compounds III are obtainable by reacting a cycloamine (V) having the desired A moiety, ie A—H in which A is as defined above, with oxalyl chloride in the presence of an acid acceptor, eg a trialkyl amine such as triethylamine, in an inert medium, eg a halogenated hydrocarbon, such as methylene chloride, at moderate temperatures, eg from about −20° to 5° C., preferably at about 0° C. (process c). The reaction requires two moles of the amine (V) for each mole of oxalyl chloride.

The compound I where X=Cl, n=1 and A is of type (a) where m=4 ie 1-(chloro-1,2-dioxopropyl)pyrrolidine, is reported in the literature, ie in Chem. Ber. 101, 3163; 3165 as Compd. 13. However, no use in combatting microorganisms is disclosed.

Those compounds I other than where X is chloro, when n is one and A is of type (a) where m is four, ie compounds of class I', are novel and constitute an embodiment of this invention.

The preparation of a Compound I may conviently be represented by Reaction Scheme A, below in which A, M, n, and X are as defined above:

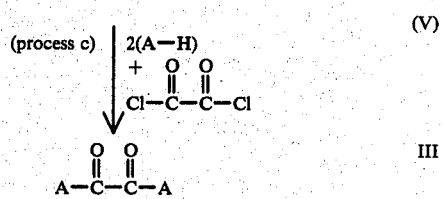

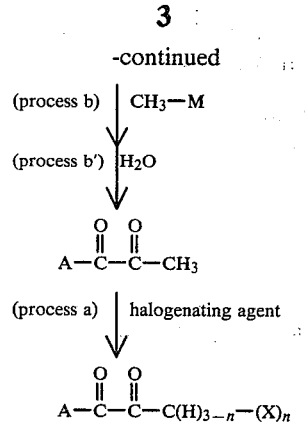

Many reactants and reagents employed in the above described reactions, eg Compounds II, III, IV and V are known, a number of which are commercially available. Those that are not known may be prepared by adaptation of methods described in the literature for the preparation of the known compounds.

The products of the processes described herein may be recovered and refined, where such is desired, by conventional means, such as by crystallization, distillation or chromatographic techniques such as column or thin layer chromatography.

In accordance with one aspect of the present invention, there is provided a method of combatting phytopathogenic fungi and bacteria in plants, seeds or soil comprising treating said plants, seeds or soil with a fungicidally or bactericidally effective amount of a compound of the formula I.

In employing the compounds of the formula I as fungicides and bactericides, and as will be appreciated, the amount of compound of formula I employed will vary depending on such factors as whether the treatment is prophylactic or therapeutic, whether the compound is applied as a foliar spray, a soil treatment or a seed dressing, the species of fungi or bacteria and the time of application. However, in general, satisfactory results are obtained when the compound is applied to a crop locus, either on crops or to soil, at a rate of from about 0.1 to 10, preferably about 0.2 to 5 kg (active ingredient)/hectare. The treatment may be repeated as required, e.g. at 8 to 30 day intervals. When employed as a seed dressing, satisfactory results are obtained when the compound is employed at a rate of from about 0.05 to 0.5, preferably about 0.1 to 0.3 g/kg seed.

The invention also provides, as an additional feature, fungicidal and bactericidal compositions, comprising, as fungicide or bactericide, a compound of formula I and an inert fungicide or bactericide carrier. The carriers may be liquids or solids.

In general, such compositions contain from about 0.01 to 90, preferably from about 0.1 to 60% by weight of active agent. They may be in concentrate form, for dilution down prior to application, or in dilute, ready to apply, form. As examples of particular forms may be given wettable powder, emulsion concentrate, dusting, spraying, granulate and delayed release forms, incorporating conventional carriers and such other diluents and/or adjuvants conventional in the agro-chemical art. Emulsion concentrate forms generally contain from about 0.1 to 50%, preferably about 1 to 25% by weight of active ingredient solid, particulate compositions are preferred. Where the carrier is a liquid, such as water, eg in compositions for spraying, it is preferred that a surface active agent be present.

The compositions particularly adapted for spraying, preferably include a surfactant such as a liquid polyglycol ether, a fatty alkyl sulphate or a lignin sulphonate.

The term "soil", as used herein is intended to embrace any conventional growing medium, whether natural or artificial.

Fungi against which the compounds of the formula I are indicated to be particularly of interest include by way of illustration the following:

(A) Basidiomycetes, comprising (A.1) those of the Order Uredinales such as those of the genus Uromyces in plants such as beans, e.g. *Uromyces appendiculatus*, and ornamentals, e.g. *Uromyces dianthi*, those of the genus Hemileia in plants such as coffee, e.g. *Hemileia vastatrix*, those of the genus Puccinia in plants such as cereals (e.g. wheat, oats, barley) e.g. *Puccinia graminis, Puccinia recondita* and *Puccinia striiformis*, or ornamentals, e.g. *Puccinia pelargoniizonalis* and *Pucc. antirrhini*, those of the genus Phakopsora in plants such as soya, e.g. *Phakopsora pachyrhizi*, those of the genus Melampsora in plants such as flax, e.g. *Melampsora lini*, and those of the genus Tranzschelia, e.g. *Tranzschelia pruni* in plums;

(A.2) those of the Order Ustilaginales such as those of the genus Ustilago in plants such as barley, wheat, corn and sugarcane, e.g. *U. maydis* on corn and *U. nuda* on barley, and (A.3) those of the genus Stereum in pip and stone fruit trees, e.g. *Stereum purpureum* in apple and prune.

(B) Ascomycetes, comprising (B.1) those of the Order Erysiphales such as those of the genus Erysiphe in plants such as cucumber, barley, wheat an sugarbeet, e.g. *Erysiphe graminis* f.sp. *tritici* on wheat and *Erysiphe cichoraceareum* on cucumbers; those of the genus Sphaerotheca on cucumbers and roses, e.g. *Sphaerotheca pannosa* on roses; those of the genus Podosphaera in apples, pears and prunes, e.g. *Podosphaera leucotricha* on apples; those of the genus Uncinula on plants such as grapes, e.g *Uncinula necator* on grapevine; those of the genus Oidium on a wide variety of plants; and those of the genus Leveillula in plants such as cotton and other Malvaceae, e.g. *Leveillula taurica* on cotton.

(C) Oomycetes, comprising (C.1) those of the genus *Phytophthora spp.*, e.g. *Ph. cactorum, Ph. parasitica* and *Ph. cinamomi* on susceptible plants; and (C.2) those of the genus Aphanomyces in plants such as pea an sugar beet, e.g. *Aphanomyces euteiches* in sugar beet, and (D) Deuteromycetes, comprising (D.1) those of the genus Helminthosporium in plants such as barley and corn, e.g. *Helm. Sativum;*

(D.2) those of the genus Septoria in plants such as wheat, tomato and celery, e.g. *Sept. tritici* in wheat;

(D.3) those of the genus Rhizoctonia in plants such as cotton and potato, e.g. *Rhiz. Solani* in cotton;

(D.4) those of the genus *Fusarium spp*, e.g. *F. oxysporum f. sp. lycopersici* in tomato, *F. oxysporum f. sp. vasinfectum* in cotton, *F. oxysporum f. sp. cubense* in banana, *F. solani* in vegetables, *F. culmorum* in cereals and *F. graminearum* in cereals;

(D.5) those of the genus Thielaviopsis in plants such as cotton, tobacco etc., e.g. *Thielaviopsis basicola* in cotton;

(D.6) those of the genus Phoma in plants such as sugar beet, rape etc., e.g. *Phoma betae* in sugar beet;

(D.7) those of the genus *Piricularia spp.*, e.g. *P. oryzae* on rice; and (D.8) those of the genus *Colletotrichum spp.*, e.g. *C. lindemuthianum* in beans; as well as

*Verticillium spp.*, e.g. *V. albo-atrum* in a wide spectrum of economically important crops such as hop, alfalfa and solanaecous crops; and

*Pythium spp.*, e.g. *P. aphanidermatum* in sugar beet.

Bacteria against which compounds I are particularly effective include those of the genus

*Xanthomonas spp.*, e.g. *X. malvacearum* in cotton *X. pelargonii* in Pelargonium; and

*Pseudomonas spp.*, e.g. *P. tomato* in tomato *P. syringae* in susceptible plants.

Fungi and Bacteria of the aforementioned genera cause considerable damage in agriculture, e.g. in tomato, cotton and cereal crops as well as in arboriculture and ornamentals, and are difficult to prevent or combat.

The preferred compound for use in the method of the invention is 1-(3-chloro-1,2-dioxopropyl)-piperidine (Example 1) and the compounds of the formula I, especially the preferred compound, are especially useful against Fusarium, Phytophthora, Ustilago, Pythium, Colletotrichum, Stereum, Thieliviopsis, Verticillium, Pseudomonas and Xanthomonas.

The fungicidal/bactericidal activity of Compounds I is indicated by conventional tests such as described below:

Test method A; In vivo test employing *Tomato wilt* (*Fusarium oxysporum f.sp. lycopersici*) *Lycopersicon esculentum* cv. 'Rheinland's Ruhm' (tomato) is cultivated in a mixture of peat and sand in planter boxes for 10 days. Vapour-sterilized peat is infested with Fusarium-inoculum and the mixture then treated by a soil mix method to give concentrations of 160, 40 and 10 ppm of active ingredient per volume of soil. After transfer of the treated, infested peat to plastic pots of 6 cm diameter, the pots are planted with tomato seedlings from the planter boxes. The plants are incubated at a temperature of 27° C. and 60–70% rH for 21 days. The efficacy of the active agent treatment is determined by comparing the degree of wilt (symptoms) with that of untreated, similarly inoculated check plants.

In the case of the compound of Example 1 a significant degree of fungicidal activity is observed.

An analogous test with similar results is run on *Pythium aphanidermatum* on cucumber.

Test method B; In vitro test employing *Ustilago maydis* (corn smut). Different concentrations of the active ingredient are incorporated in malt agar plates to give concentrations of 0.8 to 200 ppm a.i.. The plates are then inoculated by spraying a spore suspension of *U. maydis* onto them or placing an agar plug containing the fungus in the center of the plate. The plates are incubated at room temperature for 2–5 days. The efficacy of the active agent treatment is determined by comparing the growth of the fungus with that in untreated, similarly inoculated plates.

In the case of the compound of Example 1 a significant degree of fungicidal activity is observed.

Analogous tests with similar results are run on the following fungi/bacteria: *Phytophthora cactorum, Stereum purpureum, Thielaviopsis basicola Verticillium albo-atrum, Colletotrichum lindemuthianum Pseudomonas tomato* and *Xanthomonas pelargonii*.

In test analogous to in vivo and in vitro tests described above similar activity is seen when employing the compounds of Examples 2 to 9 at the higher concentrations.

In addition to the previously mentioned carrier and surface-active materials, formulations of the compound of the invention may also contain further additives with special purposes e.g. stabilizers, deactivators (for solid formulations on carriers with an active surface), agents for improving the adhesion to plants, corrosion inhibitors, anti-foaming agents and colorants.

Moreover, further fungicides, bacteriacides or other beneficially-acting materials, such as insecticides, may be present in the formulations and are contemplated as further embodiments of this invention.

Concentrate forms of compositions for fungicide use generally contain between about 2 and 80%, preferably between about 5 and 70%, by weight of a compound of formula I as active agent. Application forms of those compositions generally contain between about 0.01 and 10%, by weight of a compound of formula I as active agent.

Examples of the production of fungicide and bacteriacide formulations are as follows, wherein all parts are parts by weight, unless indicated otherwise:

(a) Granulate 5 parts of 1-(3-chloro-1,2-dioxopropyl)-piperidine dissolved in 10 parts of an aromatic solvent preferably with a boiling point within the range of 185°–213° C. The solution is sprayed onto 90 g of crushed, thoroughly sieved pumice (grain size 0.3–1 mm) by a conventional technique.

(b) Emulsion Concentrate 25 parts by weight of 1-(3-chloro-1,2-dioxopropyl)-piperidine are mixed with 30 parts of iso-octyl phenyl octaglycol ether and 45 parts of a petroleum fraction with a boiling range of 210°–280° C. ($D_{20}$:0.92). The concentrate is diluted with water to the desired concentration.

(c) Wettable powder formulation 50 parts of a compound of 1-(3-chloro-1,2-dioxopropyl)-piperidine are ground with 2 parts of lauryl sulphate, 3 parts of sodium lignin sulphonate and 45 parts of finely divided kaolinite until the average particle size is below 5 microns. The resulting wettable powder is diluted with water before use to a concentration of between 0.1% and 5% active agent. The resulting liquor may be applied as a foliar spray, or as a soil or root drench.

(d) Seed dressing 45 parts of a compound of 1-(3-chloro-1,2-dioxopropyl)-piperidine are mixed with 1.5 parts of diamyl-phenoldecaglycolether ethylene oxide adduct, 2 parts of spindle oil, 51 parts of fine talcum and 0.5 parts of colorant rhodamin B. The mixture is ground in a contraplex mill at 10,000 rpm until an average particle size of less than 20 microns is obtained. The resulting dry seed dressing powder has good adherance and may be applied to seeds, e.g. by mixing for 2 to 5 minutes in a slowly turning vessel.

Compounds I are also useful in inhibiting the undesirable growth of fungi and bacteria on painted surfaces, paper, plastic, textile, leather and wood products, by incorporating a microbe-inhibiting amount of a Compound I in such material, or by application to its surface, for example, by such well-known methods as spraying, dipping or otherwise coating the exposed surfaces of a product. By the term paint is intended to be included oil-based paints, latex-based paints and similar coatings, such as varnishes, lacquers, shellacs and drying-oils, eg linseed oil. The product of Example 10, ie 1-(3-chloro-1,2-dioxopropyl)-hexamethylenimine is particularly useful for such utility. Exemplary of the undesirable fungi and bacteria causing conditions such as mildew are Pseudomonas sp., *Aureobasidium Pullulans,* Alternaria sp. and Cladosporium sp. Suitable compositions may be prepared as is conventional in the art for inhibiting the growth of microbes in paint formulations and formulations to be applied to the surfaces of manufactured products.

In the following examples, which are illustrative of the invention, temperatures are in degrees in centigrade, and room temperature is 20° to 30° C., unless indicated otherwise.

EXAMPLE 1

1-(3-chloro-1,2-dioxopropyl)-piperidine

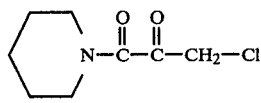

Step A Bis-(piperidine) oxamide

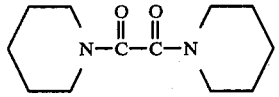

To 20.0 g of piperidine in 200 ml of methylene chloride at 0° is added 10.08 ml of oxalyl chloride, and 32.61 ml of triethylamine and the resulting mixture stirred for about 20 hours at room temperature. The reaction mixture is then washed with 200 ml portions of 5% hydrochloric acid, then 10% aqueous sodium bicarbonate and then brine. The organic phase (extract) is then dried over anh. sodium sulfate, and then concentrated under vacuum to give crude solids, which upon crystallization from methylene chloride/hexane (cold) yield the product of this step as a solid, m.p. 90°–93°.

Step B 1-(1,2-Dioxopropyl)-Piperidine

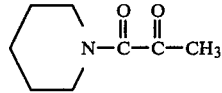

Under anhydrous conditions 38.23 ml of a 2.8 molar solution of methyl magnesium chloride (CH$_3$ Mg Cl) is added dropwise to 12.0 g of the product of Step A (molar ratio of about 4:1) in about 600 ml of dry tetrahydrofuran at +5° to 10°, with stirring. After addition is completed, stirring is continued for one hour at +15° to 20°. Cold dilute hydrochloric acid (about 6%) is then added to the reaction mixture (to quench the reaction), until complete solution is achieved. Solvent (THF) is then stripped off under vacuum, the remaining material taken up in methylene chloride (about 150 ml.) and extracted three times with aqueous sodium bicarbonate. The organic phase is then washed with brine, then dried over anh. sodium sulfate, filtered and concentrated under vacuum to an oily residue. The residue is filtered through a silica gel column (using chloroform as eluant). The filtrate is then concentrated to obtain the product of this step as a yellow oil.

Step C 1-(3-chloro-1,2-dioxopropyl)-piperidine

To a hot (50°) solution of the product of step B in 20 ml chloroform, 2.61 g (1.55 ml) of sulfuryl chloride is added dropwise (using a syringe) with vigorous stirring over a period of from 10 to 15 minutes. The mixture is stirred for about 7 hours at 50°. The mixture is then quenched by pouring into water. The resulting mixture is then extracted with methylene chloride. The combined extracts are washed with 10% aq. sodium bicarbonate solution then brine, dried over anh. sodium sulfate, then concentrated (under vacuum) to obtain an oily residue. The oil is distilled under vacuum (0.01 mm Hg) at 100° (constant boiling point) to obtain an oil which is re-distilled (at 0.001 mm Hg) at 90° C. for ½ hr. to obtain refined title product.

EXAMPLE 2

1-(3,3-dichloro-1,2-dioxopropyl)-piperidine

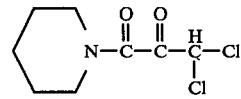

Repeating the procedure of Example 1, but in Step C, using approximately twice the amount of the sulfuryl chloride, used therein, there is accordingly obtained the title product of this example, melting at less than 50°.

EXAMPLE 3

1-(3-bromo-1,2-dioxopropyl)-piperidine

Repeating the procedure of Step C of Example 1, but replacing the sulfuryl chloride used therein with an approximately equivalent amount of bromine at 0°, there is accordingly obtained the title product, melting at below 50°.

EXAMPLE 4

Repeating the procedure of Example 1, but in Step A, replacing the piperidine used therein with approximately equivalent amounts of:

(a) pyrrolidine, or (b) morpholine, there is similarly obtained:

(a) 1-(3-chloro-1,2-dioxopropyl)-pyrrolidine (m.p. 63°–65°); and (b) 1-(3-chloro-1,2-dioxopropyl)-morpholine (as an oil).

EXAMPLE 5

Repeating the procedure of Examples 1 and Example 3, but in Step A replacing the piperidine used therein with approximately equivalent amounts of:

(a) pyrrolidine; or (b) morpholine there is similarly obtained:

(a) 1-(3-bromo-1,2-dioxopropyl)-pyrrolidine (as an oil); and (b) 1-(3-bromo-1,2-dioxopropyl)-morpholine (as an oil)).

EXAMPLE 6

Repeating the procedures of Examples 2 and 4, there is similarly obtained:
(a) 1-(3,3-dichloro-1,2-dioxopropyl)-pyrrolidine; and
(b) 1-(3,3-dichloro-1,2-dioxopropyl)-morpholine.

EXAMPLE 7

Repeating the procedure of Example 1, but using in place of the piperidine used in Step A therein, approximately twice the equivalent amount of piperazine; there is accordingly obtained: 1-(3-chloro-1,2-dioxopropyl)-piperazine.

EXAMPLE 8

Repeating the procedure of Example 1, but using in place of the piperidine used in step A, an approximately equivalent amount of 4-methylpiperazine, there is accordingly obtained 1-(3-chloro-1,2-dioxopropyl)-4-methylpiperazine.

EXAMPLE 9

1-(3,3,3-trichloro-1,2-dioxopropyl)-piperidine

Repeating the procedure of Example 1, but in Step C, using approximately triple the amount of the sulfuryl chloride, used therein, there is accordingly obtained the title product of this example.

EXAMPLE 10

1-(3-chloro-1,2-dioxopropyl)-hexamethyleneimine

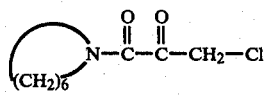

Step A Bis-(hexamethyleneimine)oxamide

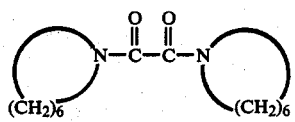

To 40.0 g of hexamethyleneimine in 250 ml of methylene chloride at 0° is added 25.4 g of oxalyl chloride, and 40.0 g of triethylamine and the resulting mixture stirred for about 20 hours at room temperature. The reaction mixture is then washed with 200 ml portions of 5% hydrochloric acid, then 10% aqueous sodium bicarbonate and then brine. The organic phase (extract) is then dried over anh. sodium sulfate, and then concentrated under vacuum to give crude solids, which upon crystallization from methylene chloride/hexane (cold) yields the product of this step as a solid, m.p. 62°-64° C.

Step B 1-(1,2-Dioxopropyl)-hexamethyleneimine

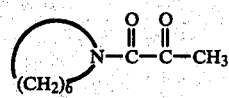

Under anhydrous conditions, 11.9 g of methyl magnesium bromide ($CH_3MgBr$) in tetrahydrofuran (dry) is added dropwise to 17.64 g of the product of Step A (molar ratio of about 4:1) in about 250 ml of dry tetrahydrofuran at +5° to 10°, with stirring. After addition is completed, stirring is continued for one hour at +15° to 20° and then reflux for 50 hrs. Cold dilute hydrochloric acid (about 6%) is then added to the reaction mixture (to quench the reaction), until complete solution is achieved. Solvent (THF) is then stripped off under vacuum, the remaining material taken up in methylene chloride (about 150 ml.) and extracted three times with aqueous sodium bicarbonate. The organic phase is then washed with brine, then dried over anh. sodium sulfate, filtered and concentrated under vacuum to an oily residue. The residue is kobelrohr distilled at 110° to 130°, at about 0.5 mm Hg to obtain the product of this step as a yellow oil.

Step C
1-(3-chloro-1,2-dioxopropyl)-hexamethyleneimine

To a solution 32 g of the product of step B in 700 ml chloroform, 30 g of sulfuryl chloride is added dropwise (using a syringe) with vigorous stirring over a period of from 10 to 15 minutes. The mixture is stirred for about 20 hours at RT. The mixture is then quenched by pouring into water. The resulting mixture is then extracted with methylene chloride. The combined extracts are washed with 10% aq. sodium bicarbonate solution, then brine, dried over anh. sodium sulfate, then concentrated (under vacuum) to obtain an oily residue. The oil is chromatographed on silica gel with 5% ethyl acetate in methylene chloride to obtain the pure product as an oil.

What is claimed is:

1. The method of combatting phytopathogenic fungus and bacteria in plants, seeds or soil comprising treating said plants, soil or seeds with a fungicidally or bactericidally effective amount of a compound of the formula:

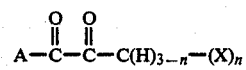

wherein
n is a whole integer of from 1 to 3,
X is halo having an atomic weight of from about 34 to 80; and
A is:

(a)

in which m is a whole integer of from 4 to 8;

(b)

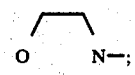

(c)

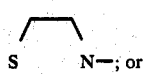

; or (d)

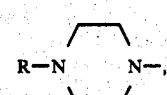

, in which R is a hydrogen atom, or alkyl having from 1 to 4 carbon atoms.

2. The method of claim 1 in which fungus is combatted.

3. The method of claim 2 in which soil is treated.

4. The method of claim 1 in which the phytopathogen is Phytophthora, Ustilago, Fusarium, Pythium, Stereum, Thielaviopsis, or Verticillium.

5. A method of claim 2 in which the compound is administered at a rate of from about 0.1 to 10 kilograms of active ingredient per hectare.

6. A method of claim 1 in which bacteria is combatted.

7. A method of claim 1 in which seed is protected against soil-borne plant diseases by applying the compound at a rate of from about 0.05 to 0.5 grams per kilogram of seed.

8. The method of any of claims 2, 6 or 7 in which the compound is 1-(3-chloro-1,2-dioxopropyl)-piperidine.

9. A method of claim 1 in which A is of type (a).

10. A method of claim 1 in which A is of type (b).

11. A method of claim 1 in which A is of type (c).

12. A method of claim 1 in which A is of type (d).

13. A method of claim 9 in which n is one.

14. A method of claim 1 in which m is from 4 to 7.

15. A fungicidal or bactericidal composition comprising an inert fungicide or bactericide carrier and a fungicidally or bactericidally effective amount of a compound of the formula:

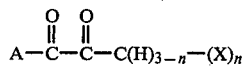

wherein n is a whole integer of from 1 to 3,

X is halo having an atomic weight or from about 34 to 80; and

A is:

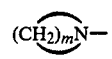 (a)

in which m is a whole integer of from 4 to 8;

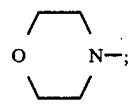 (b)

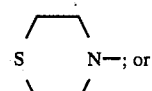 (c)

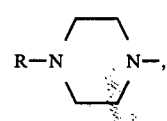 (d)

in which R is a hydrogen atom, or alkyl having from 1 to 4 carbon atoms; provided that a surfactant is present when the carrier is a liquid.

16. A composition of claim 15 in which m is from 4 to 7.

17. A composition of claim 15 or 16 in which X is other than chloro when n is one and A is of type a) in which m is four.

18. A composition in accordance with claim 15 or 16 which comprises said compound and a solid carrier, said composition being in solid particulate form.

19. A composition in accordance with claim 15 in which the compound is 1-(3-chloro-1,2-dioxopropyl)-piperidine.

* * * * *